United States Patent [19]

Yoshikawa et al.

[11] 4,169,811

[45] Oct. 2, 1979

[54] OXYGEN INDICATOR

[75] Inventors: Yoshio Yoshikawa, Ushiku; Takanari Nawata, Tokyo; Mikio Goto, Matsudo; Yuichi Fujii, Tokyo, all of Japan

[73] Assignee: Mitsubishi Gas Chemical Co., Inc., Tokyo, Japan

[21] Appl. No.: 886,638

[22] Filed: Mar. 15, 1978

[30] Foreign Application Priority Data

Mar. 23, 1977 [JP] Japan .................. 52-31730
Mar. 29, 1977 [JP] Japan .................. 52-35016
Nov. 16, 1977 [JP] Japan .................. 52-137507

[51] Int. Cl.$^2$ ............... C09K 3/00; G01N 21/12; G01N 33/02
[52] U.S. Cl. ................ 252/408; 23/230 R; 23/230 B; 73/19; 73/23; 116/206
[58] Field of Search ............ 116/114 AM, 114 P; 252/408; 23/230 R, 230 B, 232 R, 253 TP, 254 R; 73/19, 23; 195/103.5 R

[56] References Cited

U.S. PATENT DOCUMENTS

| | | | |
|---|---|---|---|
| 2,063,245 | 12/1936 | Haeseler | 23/232 R |
| 2,967,092 | 1/1961 | Buchoff et al. | 252/408 |
| 3,067,015 | 12/1962 | Lawdermilt | 116/114 AM |
| 3,451,741 | 6/1969 | Manos | 252/408 |
| 3,505,020 | 4/1970 | Caldwell | 23/230 R |
| 3,672,842 | 6/1972 | Florin | 252/408 |
| 3,681,027 | 8/1972 | Smith | 252/408 |

FOREIGN PATENT DOCUMENTS

| | | | |
|---|---|---|---|
| 495694 | 1/1974 | Japan | 23/230 R |
| 144046 | 3/1961 | U.S.S.R. | 252/408 |

OTHER PUBLICATIONS

Fildes, P. et al., Brit. J. Exp. Path., vol. 2, pp. 153–154, (1921).

*Primary Examiner*—Benjamin R. Padgett
*Assistant Examiner*—T. S. Gron
*Attorney, Agent, or Firm*—Frishauf, Holtz, Goodman & Woodward

[57] ABSTRACT

An oxygen indicator comprising at least one dyestuff, at least one alkaline substance and at least one reducing agent is disclosed.

23 Claims, No Drawings

OXYGEN INDICATOR

BACKGROUND OF THE INVENTION

This invention relates to an oxygen indicator, and particularly relates to an oxygen indicator comprising at least one dyestuff, at least one alkaline substance and at least one reducing agent. In the present oxygen indicator, the color of the oxygen indicator in an aerobic atmosphere differs from the color thereof in an anaerobic atmosphere. So, whether oxygen is present or not in the atmosphere in which the indicator is placed is easily determined by its reversible color change.

An oxygen indicator, which comprises an aqueous solution of sodium hydroxide, glucose and Methylene Blue has been known to the art.

Recently, oxygen-free packaging of foodstuffs, e.g. vacuum-package, oxygen absorption package, nitrogen-sealing package, and so on, is widely employed in order to prolong the shelf-life of the foodstuff. So, a convenient oxygen indicator which has high sensitivity and long life is necessitated for the control of such packing systems. However the life of the oxygen indicator in the prior art is too short to be used for such a purpose.

SUMMARY OF THE INVENTION

We have carried out wide research to obtain an oxygen indicator without the above disadvantages and have found an oxygen indicator which has extremely long life and high sensitivity.

An object of this invention is to provide an oxygen indicator with extremely long life.

Another object of this invention is to provide an oxygen indicator with high sensitivity to oxygen.

Still another object of this invention is to provide an oxygen indicator in which the presence or absence of oxygen in gas is indicated by a reversible color change.

This invention relates to an oxygen indicator comprising (a) at least one dyestuff selected from the group consisting of compounds represented by the formula

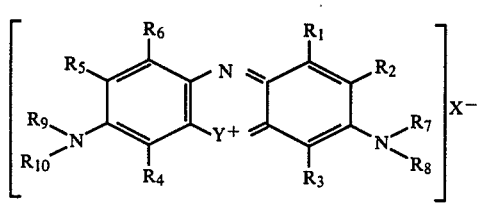

wherein $-Y^+=$ is selected from $-O^+=$, $-S^+=$ or

wherein Z is selected from hydrogen, alkyl group having 1–4 carbon atoms or aryl group having 6–7 carbon atoms; each of $R_1$–$R_6$ is independently selected from hydrogen, alkyl group having 1–4 carbon atoms, alkoxy group having 1–4 carbon atoms or nitro group; each of $R_7$–$R_{10}$ is independently selected from hydrogen, or alkyl group having 1–4 carbon atoms; and X is halogen; compounds represented by the formula

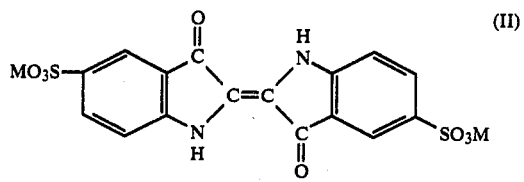

wherein M is an alkali metal and mixtures thereof; (b) at least one alkaline substance selected from the group consisting of oxides or hydroxides of alkaline earth metal; aluminum hydroxide; phosphates, carbonates or organic acid salts of alkaline earth metals; and mixtures thereof and (c) at least one reducing agent selected from the group consisting of dithionites, ferrous compounds, reducing saccharides and mixtures thereof.

DETAILED DESCRIPTION OF THE INVENTION

The term "oxygen indicator" in the claims and the specification means a material by which the presence or substantial absence of oxygen in the gaseous atmosphere surrounding the indicator is indicated by reversible color change.

Examples of the dyestuffs include Methylene Blue (C.I. Basic Blue 9) represented by the formula

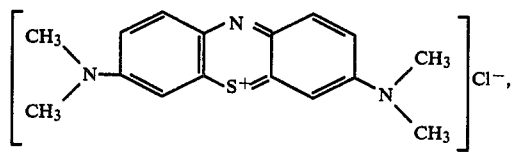

New Methylene Blue (C.I. Basic Blue 24) represented by the formula

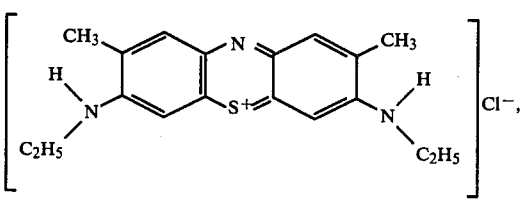

C.I. Basic Blue 3 represented by the formula

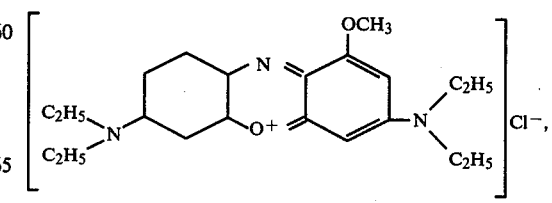

Phenosafranine represented by the formula

Capri Blue represented by the formula

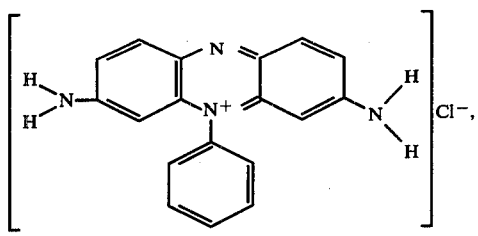

Lauth's Violet represented by the formula

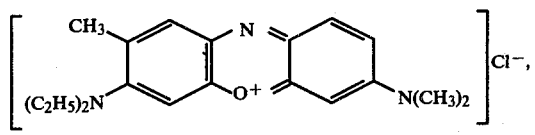

Methylene Green (C.I. Basic Green 5) represented by the formula

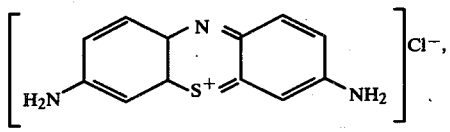

Neutral Red represented by the formula

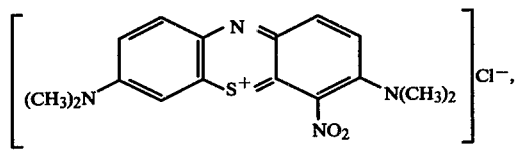

Safranine T (C.I. Basic Red 2) represented by the formulae

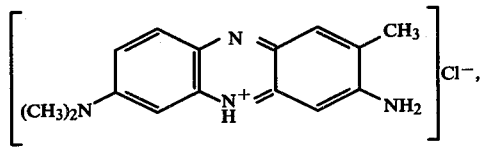

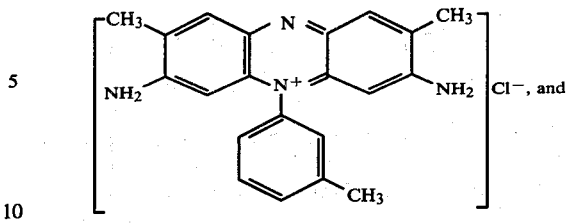

Indigo Carmine represented by the formula

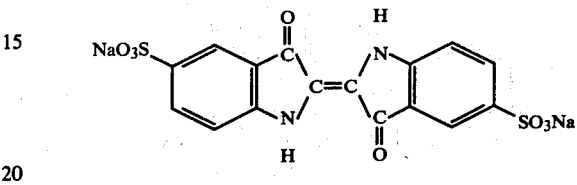

The dyestuff may be used in the form of double salt represented by, for example, Methylene Blue-FZ, Methylene Blue-SG, Methylene Blue-BH, or Methylene Blue-FZH. The compounds represented by formula (I) are preferred as dyestuffs. Methylene Blue is most preferred. One or more dyestuff is usable.

The dyestuff is employed in an amount sufficient to exhibit the function as an indicator. The amount of the dyestuff employed depends on the kinds and the amounts of other components contained in the indicator. In general, the amount of the dyestuff employed may be in the range of from 0.0001 to 5 parts, preferably from 0.001 to 1 part, per 100 parts by weight of the indicator.

Examples of the alkaline substances include hydroxides and oxides of alkaline earth metals, such as calcium hydroxide, magnesium hydroxide, calcium oxide, and magnesium oxide; aluminum hydroxide; magnesium carbonate and magnesium phosphate. Hydroxides or oxides of alkaline earth metals are preferred from the view points of life, color of the oxygen indicator and ease of solidifying the oxygen indicator. Hydroxides of alkaline earth metals are more preferred. Magnesium hydroxide is most preferred. The alkaline substance is used in an amount sufficient to maintain the pH of oxygen indicator on the alkaline side. Alkaline earth metal hydroxides, such as calcium hydroxide and magnesium hydroxide and aluminum hydroxide also serve as a carrier. Therefore, a large amount of such alkaline substance is used as a carrier.

The dithionite is a compound represented by the formula $$M_xS_2O_4$$

wherein M is monovalent or divalent cationic atom, or monovalent or divalent cationic atomic group; when M is monovalent, x is 2, and when M is divalent, x is 1. In general, it is called a hydrosulfite. Of dithionites sodium dithionite and zinc dithionite are preferred. Sodium dithionite is most preferred.

The ferrous compounds employed in the present invention include for example inorganic salts, such as ferrous sulfate, ferrous chloride or ferrous ammonium sulfate; organic salts, such as ferrous oxalate or ferrous lactate and iron sulfide. Of ferrous compounds inorganic salts, such as ferrous sulfate, ferrous chloride and ferrous ammonium sulfate are preferred from the view points of ease of availability and function of the oxygen indicator.

Reducing saccharides include, for example monosaccharides, such as mannose, glucose, fructose, erythrose and arabinose; and reducing oligosaccharides, such as maltose and lactose. Of reducing saccharides, glucose, fructose and maltose are preferred from view points of ease of availability and reducing power.

Of reducing agents, sodium dithionite, ferrous sulfate, glucose, fructose and maltose are preferred. Glucose, fructose and maltose are more preferred. Glucose and fructose are most preferred.

The reducing agent may be used in an amount sufficient to exhibit the function of an indicator. In general, the reducing agent may be used in an amount of from 0.1 to 90 parts, preferably from 1 to 50 parts, per 100 parts by weight of the indicator.

Water or an alcohol is necessary for the oxygen indicator to indicate the presence of oxygen in the gaseous atmosphere. Therefore, it is necessary that water vapor be present in the system in which the indicator is present or that the indicator contains water or an alcohol. The case in which water or an alcohol is present in the system means, for example the case in which the indicator is packed with a water-containing foodstuff.

When water vapor is present in the system in which a solid indicator is packaged, it is not necessary that the solid indicator contains water or an alcohol. However, it is preferred that the oxygen indicator contains water or an alcohol in order to increase the rate of color change.

Even if the present oxygen indicator is in a slurry state or in a state of solution, the function thereof is not lost. So, the amount of water employed is not critical. The oxygen indicator in a solid state is preferred from view points of utility, such as shelf life and ease of handling. It is preferred that the solid oxygen indicator contain water in an amount of from 0.1 to 20 parts by weight per 100 parts by weight of the whole amount of the oxygen indicator. The oxygen indicator may contain free water or a compound having water of hydration.

Compounds having water of hydration may include inorganic compounds, such as oxide, hydroxide, sulfides, halides, sulfates, nitrates, borates, phosphates, carbonates, silicates or metals; and organic acid salts; complexes, and double salts which have water of hydration in their crystal structure. Typical examples of the compounds having water of hydration include sodium carbonate decahydrate, and sodium sulfate decahydrate. The compound having water of hydration may be used alone or in the form of mixture thereof.

The alcohol compound employed in place of water or with water is one having a free alcoholic hydroxide group. Typical examples of the alcohol compounds are methyl alcohol, ethyl alcohol, glycerin, ethylene glycol, propylene glycol. Polyvalent alcohols having low volitility, such as glycerin, ethylene glycol and propylene glycol and derivatives thereof are preferred. One or more of the alcohols may be used.

The alcohol may be used with water. The amount of alcohol employed depends on whether the oxygen indicator is in a liquid or solid state and the kind of alcohol. In general, the alcohol may be used in an amount of from 0.1 to 50 parts, preferably 1 to 20 parts per 100 parts by weight of the indicator.

In general, water is preferred over an alcohol from the view points of the reaction rate and cost of the oxygen indicator. When the oxygen indicator contains water and an alcohol having a high boiling point, the alcohol serves to hold water.

The proportion of components in the present oxygen indicator is determined by the object of the use of oxygen indicator or the conditions of the use thereof.

Though the oxygen indicator can be used as it is, it is preferred for the indicator to be compressed into a shaped article such as a tablet. In case of compressing the indicator, it may contain additives such as a binder.

The oxygen indicator may be carried on a carrier for solidifying the indicator. Calcium hydroxide, magnesium hydroxide, aluminum hydroxide, calcium oxide, magnesium oxide, calcium phosphate, barium carbonate, magnesium phosphate, and magnesium carbonate which are the alkaline substances constituting the present oxygen indicator also serve as carriers. Examples of other carriers include aluminum oxide, titanium oxide, silica gel, alumina gel, synthetic zeolite, natural zeolite, kaoline, activated clay; inorganic acid salts, such as calcium sulfate, magnesium silicate, organic acid salts, such as magnesium stearate, calcium oxalate, calcium tartrate, calcium malonate, calcium benzoate; ion exchange resin; cellulose materials, such as cellulose, paper, cloth; and organic high polymers. The use of the carrier is not critical.

The present oxygen indicator comprises a dyestuff, an alkaline substance and a reducing agent, and optionally water or alcohol. Other additives, such as fillers, color additives for varying tint, such as pigments or dyes which do not interfere with the function of the oxygen indicator and the like may be added to the oxygen indicator.

The color of the present oxygen indicator depends on the kinds of components constituting the oxygen indicator.

The process used for preparing the oxygen indicator of the present invention is not critical. For example, the present oxygen indicator may be prepared by mixing a dyestuff, an alkaline substance, and a reducing agent, and optionally water or an alcohol and other additives by mechanical means.

When the present oxygen indicator is employed in a vacuum package method, nitrogen-sealing method or oxygen absorption method for preserving fresh or processed foodstuffs or preventing oxidation of organic chemicals or metals, the presence or absence of oxygen in the sealed container can be detected. Incomplete removal of gas and leakage of air due to incomplete sealing can easily be observed by using the present oxygen indicator.

Since the present oxygen indicator can be prepared in a solid state, handling of the indicator is quite easy and the indicator can be used in a wide variety of fields.

Since the present oxygen indicator is stable, it is unnecessary to store it in a cool and dark place, and it can be stored for a long time. Though life of the indicator depends on the components constituting the oxygen indicator, it can be stored for several months in air and for a period more than one year under anaerobic conditions.

The minimum oxygen concentration at which the oxygen indicator shows color change is as low as 0.1%, that is, the indicator is very sensitive to the presence of oxygen. Therefore, preservation of foodstuffs in the absence of oxygen can be controlled by using the present oxygen indicator.

The present invention is further illustrated by the following Examples and Comparative Examples. However, this invention should not be limited by these examples and comparative examples. The percent and parts in the Examples are based on weight unless otherwise specified.

EXAMPLE 1

Mixing of one hundred parts of magnesium hydroxide, 0.055 part of Methylene Blue and 3.3 parts of water was continued until the magnesium hydroxide was colored uniformly. To the resulting colored powder was added 10 parts of ferrous sulfate ($FeSO_4.7H_2O$) and the resulting mixture was blended rapidly. A portion of the resulting powder was compressed into tablets.

When the resulting blue powder and tablets were allowed to stand in a nitrogen atmosphere, (the oxygen concentration therein was 0.1%) they turned white. When oxygen was added to the atmosphere, they turned blue again.

EXAMPLE 2

The procedure of Example 1 was repeated except that 50 parts of ferrous sulfate ($FeSO_4.7H_2O$) was used. This example gave the same results as that of Example 1.

EXAMPLE 3

Mixing of one hundred parts of calcium hydroxide, 0.055 part of Methylene Blue and 3.3 parts of water was continued until the calcium hydroxide was colored uniformly. To the resulting colored powder was added 10 parts of ferrous sulfate ($FeSO_4.7H_2O$) and the resulting mixture was blended rapidly. A portion of the resulting powder was compressed into tablets.

The oxygen indicator was tested for effectiveness as in Example 1, and the results were the same as in Example 1.

EXAMPLE 4

One hundred parts of magnesium hydroxide, 10 parts of ferrous sulfate ($FeSO_4.7H_2O$), 0.05 part of Methylene Blue, 3.3 parts of water and 0.015 part of Color Index (C.I.) Acid Red 52 were mixed in the same way as in Example 1.

A portion of the resulting powder was compressed into tablets. When the resulting blue powder and tablets were allowed to stand in a nitrogen atmosphere, they turned red. When oxygen was added to the atmosphere, they turned blue.

EXAMPLE 5

The alkaline substances, the ferrous compounds, the dyestuffs and water or the alcohol as given in Table 1 were mixed.

The proportion of the components and the test method were the same as those of Example 1. The results are shown in Table 1.

Table 1

| Ferrous compound | Alkaline substance | Dyestuff | Water or alcohol | Color of oxygen indicator under aerobic conditions | under anaerobic conditions |
|---|---|---|---|---|---|
| $FeSO_4$ | $Al(OH)_3$ | Methylene Blue | Water | Blue | White |
| $FeCl_2$ | $Ca(OH)_2$ | Safranine T | " | Red | " |
| " | $Mg(OH)_2$ | New Methylene Blue | " | Blue | " |
| " | $Ca(OH)_2$ | Lauth's Violet | " | Purple | " |
| $FeSO_4 \cdot (NH_4)_2SO_4$ | $Mg(OH)_2$ | Methylene Green | " | Blue | " |
| $FeSO_4$ | $Ca(OH)_2$ | Indigo Carmine | " | " | Light Green |
| " | $Mg(OH)_2$ | Methylene Blue | Ethylene glycol | " | White |
| Ferrous lactate | $Mg(OH)_2$ | " | Propylene glycol | " | " |
| Ferrous oxalate | $Mg(OH)_2$ | " | Water | " | " |
| FeS | $Mg(OH)_2$ | " | Water | " | " |

EXAMPLE 6

Three parts of hydrosulfite 85% pure (sold under the name of Superlight PB-200 by Mitsubishi Gas Chemical Company, Inc.) 12 parts of calcium hydroxide, 0.005 part of Methylene Blue and 0.2 part of water were mixed to prepare the oxygen indicator. When the indicator was allowed to stand in a nitrogen atmosphere (oxygen concentration of 0.06%), it turned white. When oxygen was added to the atmosphere, it turned blue again.

EXAMPLE 7

An oxygen indicator having components and proportion as given in Table 2 was prepared. The indicators were tested as in Example 6. The results are shown in Table 2.

Table 2

| Alkaline substance | | Amount of hydrosulfite 85% pure (part) | Amount of Methylene Blue (part) | Amount of activated carbon (part) | Amount of water (part) | Color of oxygen indicator | |
|---|---|---|---|---|---|---|---|
| kind | amount (part) | | | | | $O_2$ concentration of more than 0.1% | $O_2$ concentration of less than 0.1% |
| $Ca(OH)_2$ | 12 | 1 | 0.005 | 0.4 | 0.2 | purple | grayish white |
| " | " | 2 | " | 0.6 | " | " | " |
| " | " | 2.5 | " | 0.8 | " | " | " |
| $Mg(OH)_2$ | " | 3 | " | " | " | blue | " |

Table 2-continued

| Alkaline substance | | Amount of hydrosulfite 85% pure (part) | Amount of Methylene Blue (part) | Amount of activated carbon (part) | Amount of water (part) | Color of oxygen indicator | |
|---|---|---|---|---|---|---|---|
| | | | | | | $O_2$ concentration of more than 0.1% | $O_2$ concentration of less than 0.1% |
| kind | amount (part) | | | | | | |
| $CaCO_3$ | " | " | " | " | " | " | " |

EXAMPLE 8

The procedure of Example 6 was repeated except that compounds having water of hydration were employed in place of water. The results are shown in Table 3.

Table 3

| Alkaline substance | | Amount of hydrosulfite 85% pure (part) | Amount of methylene blue (part) | Compound having water of hydration | | Color of oxygen indicator | |
|---|---|---|---|---|---|---|---|
| kind | amount (part) | | | kind | amount (part) | oxygen concentration of more than 0.1% | oxygen concentration of less than 0.1% |
| $Ca(OH)_2$ | 12 | 3 | 0.005 | sodium carbonate decahydrate | 0.5 | purple | grayish white |
| $Mg(OH)_2$ | " | " | " | sodium carbonate heptahydrate | " | blue | " |
| $Ca(OH)_2$ | " | " | " | sodium sulfate decahydrate | " | purple | " |
| " | " | " | " | sodium borate decahydrate | " | " | " |
| " | " | " | " | calcium chloride hexahydrate | " | " | " |
| " | " | " | " | sodium pyrophosphate decahydrate | " | " | " |
| " | " | " | " | sodium metasilicate nonahydrate | " | " | " |
| $Ca(OH)_2$ | " | " | " | manganese sulfate tetra-, penta- and hexahydrate | " | " | " |
| " | " | " | " | oxalic acid dihydrate | " | " | " |
| $Mg(OH)_2$ | " | " | " | sodium sulfate decahydrate | " | " | " |
| $Mg(OH)_2$ | " | " | " | sodium borate decahydrate | " | blue | " |

EXAMPLE 9

Twelve parts of dried calcium hydroxide, 3 parts of sodium dithionite 85% pure, 0.8 part of granular activated carbon, 0.005 part of Methylene Blue and 0.5 part of ethylene glycol were mixed to prepare the oxygen indicator. When the indicator was allowed to stand in a nitrogen atmosphere (oxygen concentration of 0.08%), it turned from purple to grayish white. When oxygen was added to the atmosphere, it turned purple again.

EXAMPLE 10

The procedure of Example 9 was repeated except that alkaline substances and alcohols as given in Table 4 were employed. The results are shown in Table 4.

Table 4

| Alkaline substance | | Amount of hydrosulfite 85% pure (part) | Amount of activated carbon (part) | Amount of methylene blue (part) | Alcohol | | Color of oxygen indicator | |
|---|---|---|---|---|---|---|---|---|
| kind | amount (part) | | | | kind | amount (part) | $O_2$ concentration of more than 0.1% | $O_2$ concentration of less than 0.1% |
| $Ca(OH)_2$ | 12 | 3 | 0.8 | 0.005 | ethylene glycol | 0.7 | purple | grayish white |
| " | " | " | " | " | propylene glycol | 0.5 | " | " |
| " | " | " | " | " | diethylene glycol | " | " | " |
| " | " | " | " | " | polypropylene glycol | " | " | " |
| " | " | " | " | " | methanol | " | " | " |
| " | " | " | " | " | ethanol | " | " | " |
| " | " | " | " | " | glycerin | " | " | " |
| " | " | " | " | " | benzyl alcohol | " | " | " |
| " | " | 1 | 0.4 | " | ethylene glycol | " | " | " |
| " | " | 0.5 | 0.2 | " | " | " | " | " |
| $Ba(OH)_2$ | " | 3 | 0.8 | " | " | " | purple | light yellow |
| $Mg(OH)_2$ | " | " | " | " | " | " | blue | grayish white |
| " | " | " | " | " | propylene glycol | " | " | " |
| $CaCO_3$ | " | " | " | " | ethylene glycol | " | " | " |
| " | " | " | " | " | ethanol | " | " | " |

EXAMPLE 11

The procedure of Example 6 was repeated except that dyestuffs and alkaline substances as given in Table 5 were employed. The results are shown in Table 5.

Table 5

| Dyestuff kind | amount (part) | Alkaline substance kind | amount (part) | Amount of hydrosulfite 85% pure (part) | Amount of water (part) | Color of oxygen indicator $O_2$ concentration of more than 0.1% | $O_2$ concentration of less than 0.1% |
| --- | --- | --- | --- | --- | --- | --- | --- |
| Capri Blue | 0.005 | Ca(OH)$_2$ | 12 | 3 | 0.2 | pink | grayish white |
| New Methylene blue | " | " | " | " | " | " | " |
| Methylene Green | " | " | " | " | " | " | " |
| Lauth's Violet | " | " | " | " | " | " | " |
| Safranine T | " | " | " | " | " | " | " |
| " | " | Mg(OH)$_2$ | " | " | " | " | " |
| Capri Blue | " | " | " | " | " | " | " |
| New Methylene Blue | " | " | " | " | " | blue | " |
| Methylene Green | " | " | " | " | " | " | " |
| Lauth's Violet | " | " | " | " | " | " | " |

EXAMPLE 12

The procedure of Example 6 was repeated to prepare the oxygen indicator except that water was not employed. When two grams of the resulting oxygen indicator and 1 gr of sanitary cotton impregnated with 5 ml of water were allowed to stand in a nitrogen atmosphere (oxygen concentration of 0.06%) in a 100 ml container, the indicator turned white. When oxygen was added to the atmosphere, it turned blue again.

EXAMPLE 13

Ten parts of magnesium hydroxide, 0.1 part of glucose, 0.005 part of Methylene Blue and 0.2 part of water were mixed to prepare the oxygen indicator. When the indicator was allowed to stand in a nitrogen atmosphere (oxygen concentration of 0.1%), it turned white. When oxygen was added to the atmosphere, it turned blue again.

EXAMPLE 14

The procedure of Example 13 was repeated except that alkaline earth metals and saccharides as given in Table 6 were employed. The results are shown in Table 6.

Table 6

| Alkaline earth metal hydroxide kind | amount (part) | Reducing gent kind | amount (part) | Amount of methylene blue (part) | Amount of water (part) | Color of oxygen indicator $O_2$ concentration of more than 0.1% | $O_2$ concentration of less 0.1% |
| --- | --- | --- | --- | --- | --- | --- | --- |
| Ca(OH)$_2$ | 10 | glucose | 0.1 | 0.005 | 0.2 | purple | white |
| Ba(OH)$_2$ | " | " | " | " | " | blue | " |
| Mg(OH)$_2$ | " | fructose | " | " | " | " | " |
| Ca(OH)$_2$ | " | " | " | " | " | purple | " |
| Ca(OH)$_2$ | " | maltose | " | " | " | " | " |
| Mg(OH)$_2$ | " | glucose | " | " | " | blue | " |

EXAMPLE 15

The procedure of Example 13 was repeated except that alcohols were employed in place of water. The results are shown in Table 7.

Table 7

| Alkaline earth metal hydroxide kind | amount (part) | Reducing agent kind | amount (part) | Methylene blue (part) | Alcohol kind | amount (part) | Color of oxygen indicator $O_2$ concentration of more than 0.1% | $O_2$ concentration of less than 0.1% |
| --- | --- | --- | --- | --- | --- | --- | --- | --- |
| Ca(OH)$_2$ | 10 | glucose | 0.1 | 0.005 | ethylene glycol | 0.4 | purple | white |
| Mg(OH)$_2$ | " | " | " | " | " | " | blue | " |
| Ba(OH)$_2$ | " | " | " | " | " | " | " | " |
| Ca(OH)$_2$ | " | " | " | " | methanol | " | purple | " |
| Mg(OH)$_2$ | " | " | " | " | " | " | blue | " |
| Ca(OH)$_2$ | " | " | " | " | glycerin | " | purple | " |
| Mg(OH)$_2$ | " | " | " | " | " | " | blue | " |
| Ca(OH)$_2$ | " | " | " | " | ethylene glycol | 0.6 | purple | " |
| Ca(OH)$_2$ | " | fructose | " | " | " | 0.4 | " | " |

EXAMPLE 16

Ten parts of magnesium hydroxide, 1 part of D-glucose, 0.005 part of Methylene Blue and 0.5 parts of water were mixed to prepare the oxygen indicator. The resulting oxygen indicator was allowed to stand in air at room temperature for three months. When the indicator was placed under anaerobic conditions, it turned white.

For comparison, 1 part of sodium hydroxide, 1 part of D-glucose, 0.005 part of Methylene Blue and 10 parts of water were mixed. One gram of sanitary cotton impregnated with 5 ml of the resulting mixture was allowed to stand in air at room temperature for one week. The remarkable discoloration occurred, and when it was placed under anaerobic condition, it did not exhibit clear color change. The use of more than 1 part of NaOH further shortened the storage life of the resulting mixture.

EXAMPLE 17

The procedure of Example 13 was repeated except that dyestuffs and alkaline earth metal hydroxides as given in Table 8 were employed. The results are shown in Table 8.

Table 8

| Dyestuff | | Amount of $Mg(OH)_2$ (part) | Amount of glucose (part) | Amount of water (part) | Color of oxygen indicator | |
|---|---|---|---|---|---|---|
| kind | amount (part) | | | | $O_2$ concentration of more than 0.1% | $O_2$ concentration of less than 0.1% |
| New Methylene Blue | 0.005 | 10 | 0.1 | 0.2 | blue | white |
| Methylene Green | " | " | " | " | " | " |
| Lauth's Violet | " | " | " | " | " | " |

EXAMPLE 18

The procedure of Example 13 was repeated to prepare the oxygen indicator except that water was not employed. Two grams of the resulting oxygen indicator and 1 gr of sanitary cotton impregnated with 5 ml of water were allowed to stand in a nitrogen atmosphere (oxygen concentration of 0.06%) in a 100 ml container, it turned white. When oxygen was added to the atmosphere, it turned blue again.

What is claimed is:

1. A solid state oxygen color-change indicator for indicating the presence or absence of oxygen in gas comprising a solid mixture of
   (a) at least one dyestuff selected from the group consisting of compounds represented by the formula

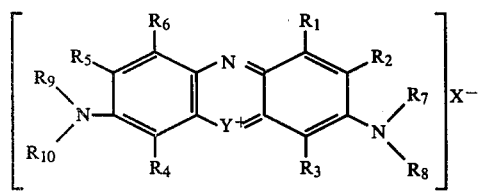

wherein $-Y^+$ is selected from the group consisting of $-O^+-$, $-S^+=$ and

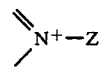

wherein Z is selected from the group consisting of hydrogen, an alkyl group having 1-4 carbon atoms and an aryl group having 6-7 carbon atoms; each of $R_1-R_6$ is independently selected from the group consisting of hydrogen, an alkyl group having 1-4 carbon atoms, an alkoxy group having 1-4 carbon atoms and a nitro group; each of $R_7-R_{10}$ is independently selected from the group consisting of hydrogen and an alkyl group having 1-4 carbon atoms; and X is halogen; compounds represented by the formula

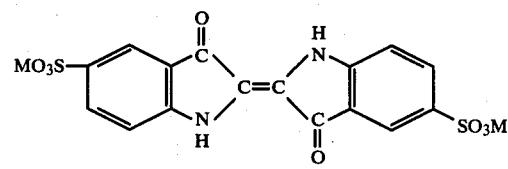

wherein M is an alkali metal; and mixtures thereof; (b) at least one alkaline material selected from the group consisting of oxides and hydroxides of alkaline earth metals; aluminum hydroxide; phosphates, carbonates, and organic acid salts of alkaline earth metals and mixtures thereof; and (c) at least one reducing agent selected from the group consisting of dithionites, ferrous compounds, reducing saccharides and mixtures thereof.

2. The oxygen indicator as defined in claim 1 wherein the dyestuff is selected from the group consisting of
   Methylene Blue (C.I. Basic Blue 9) represented by the formula

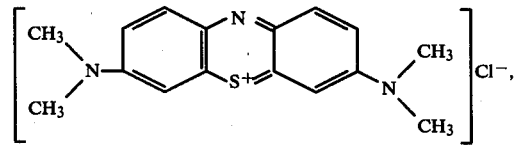

New Methylene Blue (C.I. Basic Blue 24) represented by the formula

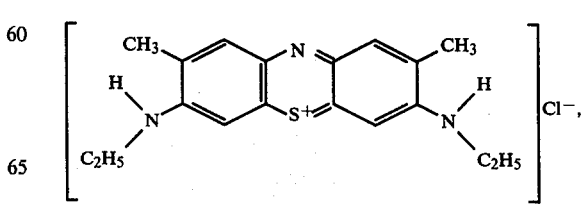

C.I. Basic Blue 3 represented by the formula

Phenosafranine represented by the formula

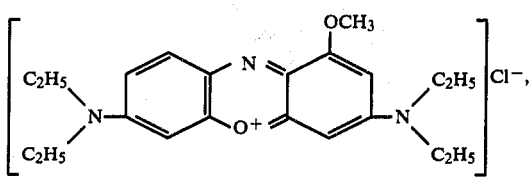

Capri Blue represented by the formula

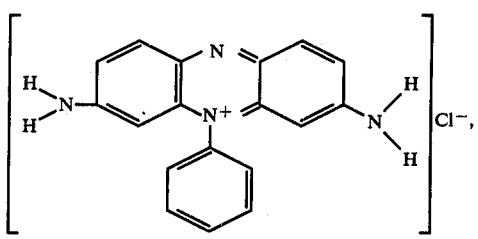

Lauth's Violet represented by the formula

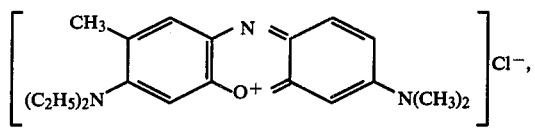

Methylene Green (C.I. Basic Green 5) represented by the formula

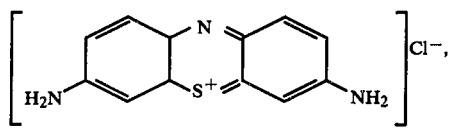

Neutral Red represented by the formula

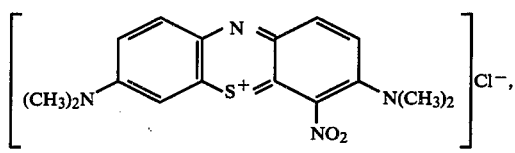

a compound represented by the formula

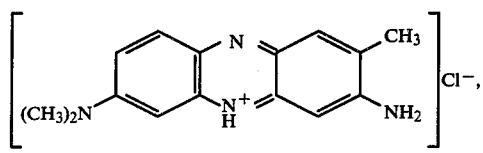

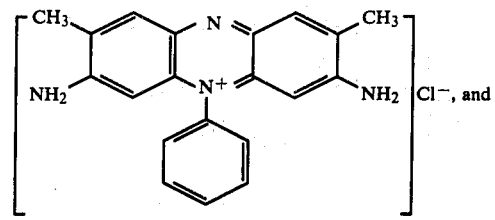

a compound represented by the formula

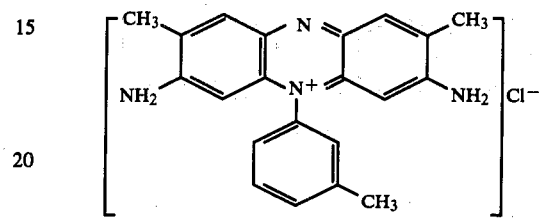

3. The oxygen indicator as defined in claim 1 wherein the dyestuff is Methylene Blue.

4. The oxygen indicator as defined in claim 1 wherein the dyestuff is used in an amount of from 0.0001 to 5 parts by weight per 100 parts by weight of the oxygen indicator.

5. The oxygen indicator as defined in claim 1 wherein the dyestuff is used in an amount of from 0.001 to 1 part by weight per 100 parts by weight of the oxygen indicator.

6. The oxygen indicator as defined in claim 1 wherein the alkaline substance is selected from the group consisting of hydroxides and oxides of alkaline earth metals.

7. The oxygen indicator as defined in claim 1 wherein the alkaline substance is selected from hydroxides of alkaline earth metals.

8. The oxygen indicator as defined in claim 1 wherein the alkaline substance is magnesium hydroxide.

9. The oxygen indicator as defined in claim 1 wherein the reducing agent is selected from the group consisting of sodium dithionite, ferrous sulfate, glucose, fructose and maltose.

10. The oxygen indicator as defined in claim 1 wherein the reducing agent is a reducing saccharide.

11. The oxygen indicator as defined in claim 1 wherein the reducing agent is selected from the group consisting of glucose, fructose and maltose.

12. The oxygen indicator as defined in claim 1 wherein the reducing agent is selected from the group consisting of glucose and fructose.

13. The oxygen indicator as defined in claim 1 wherein the reducing agent is used in an amount of from 0.1 to 90 parts by weight per 100 parts by weight of the oxygen indicator.

14. The oxygen indicator as defined in claim 1 wherein the reducing agent is used in an amount of from 1 to 50 parts by weight per 100 parts by weight of the oxygen indicator.

15. The oxygen indicator as defined in claim 1 wherein the indicator further contains water.

16. The oxygen indicator as defined in claim 1 wherein the indicator further contains at least one compound having water of hydration.

17. The oxygen indicator as defined in claim 1 wherein the indicator further contains at least one alcohol.

18. The oxygen indicator as defined in claim 17 wherein the alcohol is selected from the group consisting of methyl alcohol, ethyl alcohol, glycerin, ethylene glycol, propylene glycol, and mixtures thereof.

19. The oxygen indicator as defined in claim 1 wherein the indicator further contains water and at least one alcohol.

20. The oxygen indicator as defined in claim 19 wherein the alcohol is selected from the group consisting of methyl alcohol, ethyl alcohol, glycerin, ethylene glycol, propylene glycol, and mixtures of these alcohols.

21. The oxygen indicator as defined in claim 1 wherein the indicator is in the form of shaped article.

22. The oxygen indicator as defined in claim 1 wherein the indicator is carried on a carrier.

23. The oxygen indicator as defined in claim 1 wherein the indicator further contains a color additive for varying tint.

* * * * *